United States Patent
Mogensen et al.

(10) Patent No.: US 10,344,905 B2
(45) Date of Patent: Jul. 9, 2019

(54) INHIBITION OF BACTERIAL GROWTH IN PIPELINES

(71) Applicant: Total E&P Danmark A/S, Copenhagen Ø (DK)

(72) Inventors: Kristian Mogensen, Copenhagen Ø (DK); Trine Ljungstrøm, Copenhagen Ø (DK); Jan Larsen, Copenhagen Ø (DK)

(73) Assignee: TOTAL E&P DANMARK A/S, København Ø (DK)

( * ) Notice: Subject to any disclaimer, the term of this patent is extended or adjusted under 35 U.S.C. 154(b) by 0 days.

(21) Appl. No.: 14/917,475

(22) PCT Filed: Jul. 17, 2014

(86) PCT No.: PCT/EP2014/065459
§ 371 (c)(1),
(2) Date: Mar. 8, 2016

(87) PCT Pub. No.: WO2015/018624
PCT Pub. Date: Feb. 12, 2015

(65) Prior Publication Data
US 2016/0215920 A1    Jul. 28, 2016

(30) Foreign Application Priority Data

Aug. 9, 2013 (EP) .................................. 13179903

(51) Int. Cl.
| | | |
|---|---|---|
| *F16L 58/00* | (2006.01) | |
| *B08B 17/00* | (2006.01) | |
| *B08B 9/027* | (2006.01) | |
| *C02F 3/34* | (2006.01) | |
| *B08B 9/055* | (2006.01) | |

(Continued)

(52) U.S. Cl.
CPC .............. *F16L 58/00* (2013.01); *A01N 59/00* (2013.01); *B08B 9/027* (2013.01); *B08B 9/055* (2013.01); *B08B 17/00* (2013.01); *C02F 3/345* (2013.01); *C09K 8/54* (2013.01); *B08B 9/0555* (2013.01); *C02F 1/32* (2013.01); *C02F 1/50* (2013.01);
(Continued)

(58) Field of Classification Search
None
See application file for complete search history.

(56) References Cited

U.S. PATENT DOCUMENTS

| | | |
|---|---|---|
| 5,753,180 A | 5/1998 | Burger |
| 8,168,419 B2 | 5/2012 | Baldwin et al. |

(Continued)

FOREIGN PATENT DOCUMENTS

| | | |
|---|---|---|
| GB | 2493163 A | 1/2013 |
| WO | 2009154878 A1 | 12/2009 |

OTHER PUBLICATIONS

Rodriguez et al.; "Study of anthraquinone reaction with sodium sulphide"; The Chemical Engineering Journal 63; pp. 37-43; published Feb. 1996.*

(Continued)

*Primary Examiner* — Jeffrey T. Palenik
(74) *Attorney, Agent, or Firm* — Brinks Gilson & Lione (57) ABSTRACT

Use fresh water or water with sufficiently reduced salinity to trigger burst of bacterial cell wall due to osmotic pressure gradient. Combine the freshwater with conventional biocide treatment and pigging to increase the likelihood of killing the bacteria responsible for reservoir souring.

6 Claims, 2 Drawing Sheets

Schematic (51) Int. Cl.
*A01N 59/00* (2006.01)
*C09K 8/54* (2006.01)
*C02F 1/32* (2006.01)
*C02F 1/50* (2006.01)
*C02F 103/36* (2006.01)

(52) U.S. Cl.
CPC .... *C02F 2103/365* (2013.01); *C02F 2303/08* (2013.01); *C09K 2208/32* (2013.01)

(56) References Cited

U.S. PATENT DOCUMENTS

| | | |
|---|---|---|
| 2009/0140133 A1 | 6/2009 | Abney |
| 2009/0180992 A1 | 7/2009 | Summer et al. |
| 2012/0107051 A1* | 5/2012 | Sweeney ............... B08B 9/055 405/184.1 |
| 2012/0137752 A1 | 6/2012 | Morrow |

OTHER PUBLICATIONS

Pope D H et al. Microbiologically Influenced Corrosion Aboveground Storage Tanks, May 1, 1995.
MCAT Daily_ Difference between hypertonic, hypotonic, and isotonic, May 14, 2010.
Neal et al. "Nonchemical Bacteria-Control Process", SPE 133368, presented Oct. 18, 2010.
International Search Report and Written Opinion for PCT/EP2014/065459, dated Sep. 25, 2014.
Preliminary Report on Patentability for PCT/EP2014/065459, dated Feb. 9, 2016.
Thermophysical properties of seawater/ A review of existing correlations and data, Apr. 16, 2010.

* cited by examiner

Figure 1 – Schematic

Figure 2 – Viability of SRB and MEA after hypotonic water treatment

INHIBITION OF BACTERIAL GROWTH IN PIPELINES

RELATED APPLICATIONS

This application claims the benefit under 35 U.S.C. § 371 of the filing date of International Patent Application No. PCT/EP2014/065459, having an international filing date of Jul. 17, 2014, which claims priority to European Application No. 13179903.3, filed Aug. 9, 2013, the contents of all of which are incorporated herein by reference in their entirety.

FIELD OF THE INVENTION

The present invention relates to methods for cleaning a section of a pipeline, e.g. a pipeline situated in connection with an oil reservoir, such as methods for remediation of microbially induced corrosion in a section of a pipeline used to transport water of a certain salinity, as well as use of hypotonic water for the remediation of microbially induced corrosion.

BACKGROUND OF THE INVENTION

Corrosion of pipelines is a concern for the oil industry. It has become clear that corrosion in water injection pipelines is to a large extent caused by $H_2S$-producing bacteria. This phenomenon is commonly referred to as microbially-induced corrosion (MIC).

Some of the bacteria responsible for corrosion belong to a group of sulphate-reducing bacteria (SRB), which are active under anaerobic conditions. Sulphate-reducing bacteria convert sulphate ($SO_4^{2-}$) to hydrogen sulphide ($H_2S$). SRB's can be found in almost all natural environments such as soils, fresh and marine waters, hot springs, geothermal areas, oil and gas wells, and in sewage systems.

In addition to induced corrosion of surface facilities, production of $H_2S$ causes reservoir souring requiring additional safety precautions at the production side. Consequently, there is a need to reduce the $H_2S$ production in a reservoir setting.

The sulphate-reducing bacteria are sessile, i.e. they grow on surfaces, and protect themselves by forming biofilms, which cause bio-fouling if not properly removed. Inhibiting the growth of SRB's and other $H_2S$-producing bacteria is therefore a matter of importance for the oil industry.

In the oil industry, pipelines may be cleaned mechanically by pigging the pipeline. This involves inserting a device (called a pig) with blades or brushes in a pipeline for cleaning purposes. The pressure of a stream of oil or water behind pushes the pig along the pipeline to clean out rust, wax, scale, and debris such as biofilms. Pigging the pipeline is only partly effective in reducing the $H_2S$-producing bacteria.

In the oil industry, cleaning of pipelines have been attempted chemically by adding commercial biocides such as formaldehyde, glutaraldehyde or tetrakishydroxymethyl phosphonium sulphate (THPS) are, or have been, used in water injection pipelines to inhibit growth of microorganisms. These chemicals are typically expensive, can be dangerous to handle, may have a negative impact on the environment and are only partially efficient in controlling bacterial growth in biofilms.

In the oil industry, cleaning of pipelines have been attempted biologically as described in U.S. Pat. No. 8,168,419 (to Baldwin et al.), which discloses prevention and remediation of petroleum reservoir souring and corrosion by treatment with virulent bacteriophage. A bacteriophage (phage) is a virus, which infects only prokaryotic cells (cells without a nucleus), such as bacteria, while leaving mammalian (e.g. human) cells unharmed. These bacteriophages must be adapted to the specific type of bacteria that is to be removed.

Finally, cleaning drinking water has been attempted using radiation. Treatment of drinking water with ultraviolet (UV) light is a method, which has been in use since 1955. More recently, it has been adopted by the oil industry during hydraulic fracturing operations, see Neal et al. "Nonchemical Bacteria-Control Process" (2010) SPE 133368. The bacteria will absorb UV light causing their DNA to undergo physical changes preventing further cell replication. While treatment with UV light is a non-chemical disinfection method, it suffers the drawback that in order to be effective the water has to be clear without any suspended solids or hydrocarbons for this mechanism to have optimum effect. Furthermore, UV radiation has not been deployed on a continuous basis.

Accordingly, there exists a need in the art for overcoming one or more of the deficiencies described in the prior art.

SUMMARY OF THE INVENTION

The present invention was made in view of the prior art described above, and the object of the present invention is to provide a method that does not suffer from one or more of the drawbacks of the prior art.

To solve the problem, the present invention provides a method for remediation of microbially induced corrosion in a section of a pipeline, such as a pipeline situated in connection with an oil reservoir, used to transport water with a total dissolved salt concentration of at least 0.25 M expressed as sodium chloride dissolved, the pipeline having a volume, where bacteria that induce corrosion grow on the inside surface of the pipeline and have an intracellular tonicity, comprising: a) performing a pig run in the section of the pipeline; b) subjecting the inside of the section of the pipeline to a hypotonic water compared to the intracellular tonicity of the bacteria growing on the inside surface of the pipeline sufficient to cause osmotic lysis in the bacteria.

That is, the inventors of the present invention in a first aspect of the invention found that bacteria living in pipes where the salt concentration is of some magnitude can be killed by osmotic lysis, which may involve first mechanically scraping the inside of the pipe, e.g. with a pig and subjecting the bacteria remaining in the pipe to a hypotonic water compared to the tonicity of the bacteria. These bacteria lyse when shock-treated with fresh water because the salinity difference between the inside of the cell and its surroundings gives rise to sudden changes in osmotic pressure.

Accordingly, use of a hypotonic water for remediation of microbially induced corrosion in a section of a pipeline situated in connection with an oil reservoir or a section thereof, the pipeline being used to transport water with a total dissolved salt concentration of at least 0.25 M expressed as sodium chloride dissolved, the pipeline having a volume, where bacteria that induce corrosion grow on the inside surface of the pipeline and have an intracellular tonicity that is at least 3-fold higher than the hypotonic water; is also provided.

The purpose of the invention described in the detailed description is to reduce microbial-induced corrosion of pipelines while reducing or eliminating the need for biocides or other treatment regimens as described in the background section by treating a pipeline with one or more pulses of low-salinity water, such as fresh water, and possibly together with biocides, bacteriophages tailored to infect the specific cells present in the biofilms, and/or other treatment regimens.

In some embodiments of the present invention, the bacteria are halotolerant or halophilic bacteria.

In some embodiments of the present invention, the tonicity of the hypotonic water is 0.1 M or less. In some embodiments of the present invention, the hypotonicity of the water is at least half the intracellular tonicity of the bacteria.

In some embodiments of the present invention, the bacteria are sulphate-reducing bacteria.

In some embodiments of the present invention, under step b) above the inside of the section of the oil reservoir pipeline is subjected to one or more pulses of hypotonic water.

In some embodiments of the present invention, the section of the tube is in contact with hypotonic water for at least 1 minute, such as at least 60 minutes.

Figure 1:
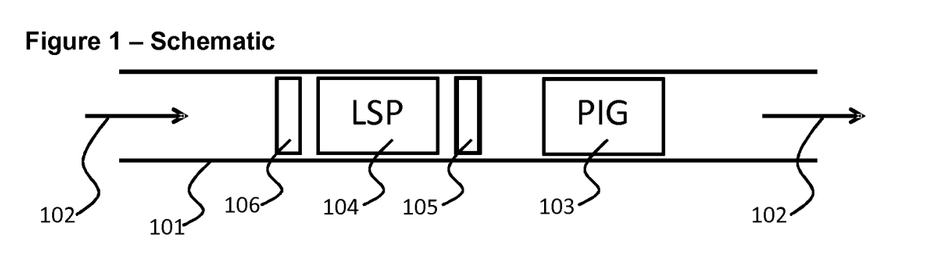
FIG. 1 shows a section of a pipe (101) with a flow in the direction of the arrows (102), and exemplifying a step of using a pigging device (103) and of injecting a low-salinity pulse (104) with optionally a leading plug (105) and optionally a trailing plug (106).

In some embodiments of the present invention, the one or more pulses of hypotonic water are enclosed by a plug on the leading (105) end of the pulse of hypotonic water, and/or by a plug on the trailing end (106) of the pulse of hypotonic water.

In some embodiments of the present invention, the plug is liquid and has a viscosity of more than 2, such as between 2 to 10 cP.

In some embodiments of the present invention, the one or more pulses of hypotonic water each have a volume of 20% or less of the volume of the section of the pipeline.

In some embodiments of the present invention, the volume of the section of the pipeline is at least 15 m$^3$.

In some embodiments of the present invention, one or more additives are added to the hypotonic water, the one or more additives selected from the list consisting of: chemical biocides and/or bacteriophages.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

Microbially induced corrosion (MIC) occurs on the inside of the pipes, where the bacteria, such as sulphate-reducing bacteria (SRB) reside, and in particular MIC occurs behind biofilms in the pipes.

SRB can be found in almost all natural environments, including seawater, and oil- and gas wells. Active participation of SRB in corrosion of metals exposed to seawater is well recognized.

The seawater salinity in the North sea and in the Middle East is around 34-36 ppt total dissolved salts (corresponding to around 0.58-0.62 M expressed as NaCl dissolved), and the microorganisms, such as SRB living in such environments are adapted to this high salinity, in that the osmotic pressure of the cytoplasm in these bacteria are balanced according to the salinity of the environment. It may be said that the high salinity water has become isotonic with respect to these microorganisms.

In an aspect of the present invention, a method for remediation of microbially induced corrosion in a pipe is provided, which may be accomplished by removing and/or killing as many of the bacteria that induce corrosion from the inside of the pipe. The remediation may be done during a maintenance sequence, which may involve at least mechanically disrupting the bacteria that grow on the inside of the pipe followed by contacting the inside of the pipeline with hypotonic water compared to the intracellular tonicity of the bacteria growing on the inside surface of the pipeline, in that the hypotonic water should be sufficiently hypotonic to cause osmotic lysis in the bacteria.

In some embodiments the remediation may be done during a maintenance sequence, which may involve contacting the inside of the pipeline with hypotonic water compared to the intracellular tonicity of the bacteria growing on the inside surface of the pipeline, in that the hypotonic water should be sufficiently hypotonic to cause osmotic lysis in the bacteria.

The whole length of the pipe or sections thereof may be remediated. In some instances the pipe may be a pipeline situated in connection with an oil reservoir or a section thereof, which is referred to in this document as an oil reservoir pipeline. An oil reservoir pipeline may be a pipeline involved in the production of oil and/or gas by transporting fluids.

The pipe is used to transport fluids comprising water, such as aqueous solutions, suspensions, emulsions and the like. In the case of an oil reservoir pipeline, the pipe may for example be used to transport oil, produced water, or injection water. In some embodiments the pipe is involved in the transport of fluids to, from and/or between offshore oil- and/or gas wells.

The pipe may have the unwanted bacteria attached to the inside surface, i.e. the bacteria that induce corrosion grow on the inside surface of the pipeline.

These bacteria should be bacteria that are adapted to a certain minimum salinity, which may be bacteria residing in pipes used to transport heavily brackish water, which may have a salinity of 0.25 M to 0.5 M expressed as sodium chloride dissolved, or in pipes used to transport sea water, which may have a salinity of 0.5 M to 0.9 M expressed as sodium chloride dissolved, or in pipes used to transport brines, which may have a salinity of 0.9 M or more (which may be up to 8 M or more) expressed as sodium chloride dissolved.

In some embodiments the salinity of the fluids will be that of heavily brackish water, seawater, or brines. In some embodiments the salinity of the fluids that the bacteria in the pipes have adapted to may have a total dissolved salt concentration of at least 0.25 M expressed as sodium chloride dissolved, such as e.g. a total dissolved salt concentration of at least 0.3 M, at least 0.35 M, at least 0.4 M, at least 0.5 M expressed as sodium chloride dissolved.

While not wanting to be bound by any theory, the inventors have found that bacteria that resides in pipes used to transport fluids of a certain minimum salt concentration will either be bacteria that are halophilic in that they require NaCl for growth or bacteria which have adapted to the saline environment, which are said to be halotolerant, and grow under saline conditions. For example the halotolerant or halophilic bacteria may have adapted to a saline environment in pipes where there is a flow of sea water of varying salinity, but having a minimum salinity of e.g. 0.25 M. For the purpose of the present application it is considered that the intracellular tonicity of these bacteria is isotonic with respect to the fluids of the certain minimum salt concentration. That is, for the purpose of the present application the halotolerant or halophilic bacteria that may have adapted to a saline environment in pipes where there is a flow of sea water of varying salinity, but having a minimum salinity of e.g. 0.25 M are considered to have an intracellular tonicity of at least 0.25 M.

The pipes used to transport fluids of a certain minimum salt concentration should have been used for a time sufficient to allow halophilic bacteria to grow on the surface, or to induce halotolerability in bacteria growing on the surface. This may vary depending on the circumstances. In some examples the pipes will have been used to transport fluids of a certain minimum salt concentration for days, such as weeks, months or years. In some embodiments the pipes used to transport fluids of a certain minimum salt concentration have been in use and have transported such fluids for several years. As also explained herein it is relevant that the bacteria to be removed has a tonicity that is different from the tonicity of the hypotonic water so that the bacteria will lyse due to osmosis.

In some embodiments of the present invention, the bacteria may be halotolerant or halophilic bacteria, such as slightly halophilic or halotolerant (may live in 0.3 to 0.8 M NaCl), moderately halophilic or halotolerant (may live in 0.8 to 3.4 M NaCl) or extreme halophilic or halotolerant (may live in 3.4 to 5.1 M NaCl).

The present invention may advantageously be used in long pipelines, as well as in large volume pipelines. The pipeline has a volume defined by the length of the pipe and the inner diameter (ID) of the pipe.

Pipelines may be of varying lengths from 10 to 100 m or smaller to more than 300 km, such as—more than; less than; or between any two of: 0.25 km, 0.5 km, 1 km, 2 km, 3 km, 4 km, 5 km, 6 km, 7 km, 8 km, 9 km, 10 km, 11 km, 12 km, 13 km, 14 km, 15 km, 16 km, 17 km, 18 km, 19 km, 20 km, 21 km, 22 km, 23 km, 24 km, 25 km, 26 km, 27 km, 28 km, 29 km, 30 km, 31 km, 32 km, 35 km, 40 km, 45 km, 50 km, 55 km, 60 km, 65 km, 70 km, 75 km, 80 km, 85 km, 90 km, 95 km, 100 km, 125 km, 150 km, 175 km, 200 km, 225 km, 250 km, 275 km, 300 km, 325 km, 350 km, 400 km. Both sections of as well as whole pipelines may be subjected to the remediation of the present invention. In some embodiments the pipelines have a length of between 1 km to 15 km, such as between 8 km to 15 km, where the inner surface of the pipes are large, and thus entails the risk that a large surface can be covered by bacteria according to the invention, which for e.g. SRB bacteria will entail a significant souring of the fluids of the pipe due to $H_2S$ pollution.

The pipelines may be of varying inner diameters from approximately 5 cm (2 inches) or smaller to approximately 61 cm (24 inches) or larger, such as: more than; less than; or between any two of: approximately 5 cm (2 inches), approximately 10 cm (4 inches), approximately 15 cm (6 inches), approximately 20 cm (8 inches), approximately 25 cm (10 inches), approximately 30 cm (12 inches), approximately 35 cm (14 inches), approximately 40 cm (16 inches), approximately 45 cm (18 inches), approximately 50 cm (20 inches), approximately 55 cm (22 inches), approximately 61 cm (24 inches), approximately 71 cm (28 inches), approximately 81 cm (32 inches), approximately 91 cm (36 inches), approximately 102 cm (40 inches), approximately 122 cm (48 inches), approximately 142 cm (56 inches), approximately 152 cm (60 inches), approximately 163 cm (64 inches), approximately 173 cm (68 inches), approximately 183 cm (72 inches), approximately 203 cm (80 inches). In some embodiments the pipelines have an inner diameter of between approximately 5 cm to 61 cm (2 to 24 inches). In some embodiments the pipelines have an inner diameter of between approximately 20 cm to 81 cm (8 to 32 inches).

The volume of the pipeline or the section of the pipeline may in some embodiments be at least 10 $m^3$, such as at least 30 $m^3$, such as at least 100 $m^3$, at least 200 $m^3$, at least 300 $m^3$, at least 500 $m^3$. For example it may be a volume between 100 $m^3$ to 2000 $m^3$, or a volume between 10 $m^3$ to 100 $m^3$ The method according to the present invention may be well suited for longer sections of pipe, consequently in some embodiments the section of pipeline to be cleaned is between 0.25 km to 25 km, such as between 1 km to 20 km, such as between 2 km to 15 km. Pipeline of this length may in some embodiments have an inner diameter of 15 to 50 cm, or correspond to between 6 to 20 inches and having a volume between 5 and 5000 $m^3$. For example between 500 and 5000 $m^3$.

The bacteria responsible for the microbially induced corrosion may protect themselves by forming a biofilm.

In some embodiments of the present invention the method of remediating microbially induced corrosion involves taking out the pipeline or section of pipeline for maintenance. The maintenance may in some embodiments involve: a) a mechanical disruption of the bacteria and/or biofilm thereby physically damaging the biofilm structure followed by b) subjecting the inside of the section of the oil reservoir pipeline to a hypotonic water compared to the intracellular tonicity of the bacteria growing on the inside surface of the pipeline sufficient to cause osmotic lysis in the bacteria.

The maintenance may in some embodiments skip the mechanical disruption and comprise b) subjecting the inside of the section of the oil reservoir pipeline to a hypotonic water compared to the intracellular tonicity of the bacteria growing on the inside surface of the pipeline sufficient to cause osmotic lysis in the bacteria.

In preferred embodiments the maintenance sequence involves: a) performing a pig run in the section of the oil reservoir pipeline; followed by b) subjecting the inside of the section of the oil reservoir pipeline to a hypotonic water compared to the intracellular tonicity of the bacteria growing on the inside surface of the pipeline sufficient to cause osmotic lysis in the bacteria.

A pig run is when a pig travels through a section of a pipeline to be cleaned. A pig (or pigging tool) is well-known in the oil industry, and is a device used for mechanical disruption of the inside of the pipeline. Pigs come in many shapes and sizes, and may be fitted with elements that assist with the mechanical disruption, such as, but not limited to blades or brushes. Pigs are also called scraper tools. The pig may have many different shapes, such as having a concave nose, for example bull nose shaped or bullet shaped, and it may be pushed by water in the pipe in the direction of normal flow. The pig may in some embodiments be made to fit the size of the pipe to be cleaned, i.e. it should not be so large that it will get stuck inside the pipe, nor should it be much smaller than the inner diameter of the tube to be cleaned, as the mechanical disruption by the pig to the sides of the pipe may be diminished.

Running a pig according to the present invention may involve using the pig to mechanically remove or disrupt biofilm and/or other foreign matter from the inside of pipes. This mechanical disruption works together with the hypotonic water by allowing the hypotonic water better access to the remaining bacteria.

In some embodiments of the present invention the above steps of a) performing a pig run; and b) subjecting the inside of the pipeline to a hypotonic water may be combined in a single step, where the fluid used to push the pig through the pipeline may be hypotonic water.

Hypotonic water refers to fluids comprising water, such as aqueous solutions, suspensions, emulsions and the like, which fluid has a tonicity that is sufficiently low compared to the intracellular tonicity of the bacteria growing on the inside surface of the pipeline to cause osmotic lysis in the bacteria.

It is desirable to have as large a difference between intracellular tonicity of the bacteria and the hypotonicity of the fluid flowing in the pipe, as such a fluid will be most effective in killing the bacteria by osmotic lysis, i.e. where the water flows into the bacterial cells in an attempt to equalise pressure between the inside and outside of the bacteria ultimately failing by bursting of the bacterial cell wall.

The difference between intracellular tonicity of the bacteria and the hypotonicity of the fluid flowing in the pipe that is sufficient to cause osmotic lysis in the bacteria depends on a number of variables, such as the type of bacteria and the intracellular tonicity of the bacteria. Pure distilled water will always provide the largest difference in tonicity. Nevertheless, other, less pure, sources of water may readily be available at the location of the pipe, and it may be economically feasible to use that source of water. For instance the source of water may be sea water itself. This seawater may undergo a desalination or reverse osmosis step to reduce the salt content sufficiently to prepare a hypotonic fluid.

The hypotonicity of the fluid that is sufficient to cause osmotic lysis in the bacteria may be determined by taking a sample of the bacteria from the pipe that is to undergo remediation of microbially induced corrosion, and culture it in a medium of the same salinity as where the sample is taken from. The number of bacteria may be visualised by e.g. staining, and a number of bacterial samples may then be subjected to hypotonic fluids of varying tonicity to determine which hypotonicity that is sufficient to cause osmotic lysis. This may be ascertained by visualizing live and dead bacteria by e.g. staining and measuring the number of live and dead bacteria after subjecting them to the hypotonic fluids.

In some embodiments of the present invention, the hypotonicity of the fluid is considered to be sufficient to cause osmotic lysis in the bacteria when more than 50% of the bacteria are dead after exposure to a hypotonic fluid, such as more than 75% of the bacteria are dead. In other embodiments the bacterial count is reduced by at least two orders of magnitude. In some embodiments the bacteria is sulphate-reducing bacteria, and the hypotonicity of the fluid that is considered to be sufficient to cause osmotic lysis in the SRB is when more than 50% of the SRB are dead after exposure to a hypotonic fluid, such as more than 75% of the SRB are dead. This can be measured using various methods, one example being $H_2S$ production. In some examples, when determining which hypotonicity that is sufficient to cause osmotic lysis, it is necessary to exclude other sources that may kill bacteria, which is not present in the fluids that is usually transported in the pipes, such as e.g. biocides. In some embodiments a method of determining which hypotonicity that is sufficient to cause osmotic lysis may be adapted from example 1, and may relate to either bacterial count and/or $H_2S$ production. In some embodiments the hypotonic water is devoid of other additives that kill bacteria, such as for example biocides.

In some embodiments of the present invention, the hypotonicity of the water is at least half the intracellular tonicity of the bacteria, such a 3-fold lower. For the purpose of the present application it is considered that the intracellular tonicity of these bacteria is isotonic with respect to the tonicity of the fluids that flows in pipes. For example, if the pipe is used to transport sea water to an injection well, and that this seawater has a total dissolved salt concentration of e.g. between 0.5 M and 0.7 M expressed as sodium chloride dissolved—then it is considered that the intracellular tonicity of these bacteria is isotonic with respect to between 0.5 M and 0.7 M. When the hypotonicity of the water is at least half the intracellular tonicity of the bacteria of the example this means that the water may have a hypotonicity of between 0.25 M and 0.35 M or lower. In some embodiments of the present invention the average total salt concentration of the fluid in the pipe is used, and in some embodiments the lowest total salt concentration is used when determining the salt concentration of the fluids in the pipes. In some embodiments of the present invention, the hypotonicity of the water is 50% or less (i.e. half) of the intracellular tonicity of the bacteria, such as 40% or less, 30% or less, 25% or less, 20% or less, 15% or less, 10% or less, 5% or less, 1% or less.

In some embodiments of the present invention, the tonicity of the hypotonic water is 0.1 M or less, such as 0.05 M or less, 0.04 M or less, 0.02 M or less, 0.01 M or less, 0.005 M or less expressed as sodium chloride dissolved.

In some embodiments of the present invention, the section of the tube is in contact with hypotonic water for at least 10 seconds, such as at least 30 seconds, such as at least 1 minute to induce osmosis in the bacteria. In some embodiments it is desirable to increase the exposure time to the hypotonic water. Accordingly, in some embodiments the exposure time may be at least 10 minutes, such as at least 15 minutes, at least 30 minutes, at least 45 minutes, or at least 60 minutes. The exposure time can be controlled in various ways.

The exposure time may for example be controlled by the flow speed of the hypotonic water, such as the volume injected per hour.

If the hypotonic water is not readily at hand, i.e. if it requires to be transported over some distance by e.g. ship to reach the pipe to be remediated, or if it needs to be manufactured on site using e.g. desalination equipment, then the cost of remediation of the pipe using hypotonic water can be reduced by reducing the amount of water injected.

Accordingly, the exposure time may be controlled by the injected amount, such as in some embodiments of the present invention, where one or more pulses of hypotonic water are injected, a number of pulses can be injected, such as 1, 2, 3, 4, 5, 6, 7, 8, 9 or 10 pulses. In some embodiments of the present invention, the one or more pulses of hypotonic water each have a volume of 20% or less of the volume of the section of the oil reservoir pipeline. In some embodiments the exposure time may be at least 10 seconds, such as at least 30 seconds, at least 1 minute, at least 10 minutes, such as at least 15 minutes, at least 30 minutes, at least 45 minutes, or at least 60 minutes. In some embodiments the exposure time is 1-10 hours. In some embodiments the exposure time may be between 10 seconds and 10 minutes, such as between 30 seconds and 5 minutes.

The exposure or contact time may additionally be controlled by a combination of flow speed and the injected amount.

Some embodiments of the present invention relates to pipelines with a volume of more than 1000 m³, which undergo one or more pulses of hypotonic water with a volume of between 10% to 30% of the total volume, i.e. more than 100 to 300 m³. If for example an injection pipeline is to be remediated and having an injection rate of more than 16000 m³/day. This would result in an exposure time of around 10-30 minutes. This exposure time can be increased if the injection rate is lowered. Another way of increasing the exposure time would be by enveloping the individual pulse of hypotonic water with a viscous spacer, denoted a plug, before and/or after the pulse of hypotonic water. The plug may be a solid, such as the pig tool or in some embodiments it may be a viscous fluid, such as e.g. a gel, with a viscosity of more than 2 cP, such as between 2 and 5 cP, such as between 2 and 10 cP, such as between 10 and 1000 cP, or more, e.g. 10 to 100 cP, such as between 2 and 20 cP. The enveloping of each individual pulse of hypotonic water has the additional effect that it limits the dispersion of the hypotonic water.

Accordingly, in some embodiments of the present invention, the one or more pulses of hypotonic water are enclosed by a plug on the leading (105) end of the pulse of hypotonic water, and/or by a plug on the trailing end (106) of the pulse of hypotonic water. The plug may be a liquid and be immiscible with water or sparingly miscible with water. It may be a hydrocarbon-containing plug, such as oil. In some embodiments the plug may be a liquid gel such as water-soluble viscous flowing gel. The gels may in some specific examples be based on or contain hydrolyzed polyacrylamide, partially hydrolyzed polyacrylamide or a colloidial dispersion gel (CDG). For example, a copolymer of acrylamide and sodium acrylate (HPAM) or polyhydroxypropyl acrylate (PHPA). In some embodiments of the present invention, the plug is liquid or a liquid gel and has a viscosity of more than 2 cP, such as between 2-10 cP.

In some embodiments of the present invention, the bacteria are sulphate-reducing bacteria (SRB). The SRB group of bacteria is a group of bacteria that reduces sulfates to sulfides, thereby releasing hydrogensulfide. In some embodiments, SRB comprise the family Desulfovibrionaceae, and in some embodiments the Desulfovibrionaceae is selected from the group consisting of *D. vulgaris, D. salixigens, D. sulfuricans, D. desulfuricans, D. postgatei, D. africanus, D. baculatus, D. gigas, D. halophilus, D. magneticus, D. multispirans, Desulfovibrio sp., D. aespoeensis,* and *D. pigra.*

In some embodiments of the present invention, the bacteria may be Methanogenic Archaea (MEA). The MEA group of bacteria is a group of bacteria that reduces $CO_2$ to methane thereby releasing a noxious gas. In some embodiments, MEA are selected from the group consisting of: *Methanobacterium bryantii, Methanobacterium formicum, Methanobrevibacter arboriphilicus, Methanobrevibacter gottschalkii, Methanobrevibacter ruminantium, Methanobrevibacter smithii, Methanocalculus chunghsingensis, Methanococcoides burtonii, Methanococcus aeolicus, Methanococcus deltae, Methanococcus jannaschii, Methanococcus maripaludis, Methanococcus vannielii, Methanocorpusculum labreanum, Methanoculleus bourgensis (Methanogenium olentangyi & Methanogenium bourgense), Methanoculleus marisnigri, Methanofollis liminatans, Methanogenium cariaci, Methanogenium frigidum, Methanogenium organophilum, Methanogenium wolfei, Methanomicrobium mobile, Methanopyrus kandleri, Methanoregula boonei, Methanosaeta concilii, Methanosaeta thermophila, Methanosarcina acetivorans, Methanosarcina barkeri, Methanosarcina mazei, Methanosphaera stadtmanae, Methanospirillium hungatei, Methanothermobacter defluvii (Methanobacterium defluvii), Methanothermobacter thermautotrophicus (Methanobacterium thermoautotrophicum), Methanothermobacter thermoflexus (Methanobacterium thermoflexum), Methanothermobacter wolfei (Methanobacterium wolfei), Methanothrix sochngenii.*

In some embodiments of the present invention, one or more additives are added to the hypotonic water, the one or more additives selected from the list consisting of: chemical biocides and/or bacteriophages.

In some embodiments of the present invention the method for remediating microbially induced corrosion involves taking out the pipeline or section of pipeline for maintenance. The maintenance may in some embodiments involve: a) a mechanical disruption of the bacteria and/or biofilm, such as a pig run, thereby physically damaging the biofilm structure followed by b) subjecting the inside of the section of the oil reservoir pipeline to a hypotonic water compared to the intracellular tonicity of the bacteria growing on the inside surface of the pipeline sufficient to cause osmotic lysis in the bacteria, and c) subjecting the inside of the section of the oil reservoir pipeline to one or more additives selected from the list consisting of: chemical biocides and/or bacteriophages.

In some embodiments of the present invention, where one or more pulses of hypotonic water are injected, one or more pulses of more additives selected from the list consisting of: chemical biocides and/or bacteriophages may be interspersed between the one or more pulses of hypotonic water.

Thus in some embodiments the following sequence is envisaged:

Mechanical disruption of the bacteria and/or biofilm followed by;
1) hypotonic water; chemical biocide treatment; or
2) hypotonic water; bacteriophage treatment; or
3) bacteriophage treatment; hypotonic water; or
4) chemical biocide treatment; hypotonic water; or
5) bacteriophage treatment; hypotonic water; chemical biocide treatment
6) chemical biocide treatment; hypotonic water; bacteriophage treatment; or
7) combinations of 1) to 6), optionally with a mechanical disruption of the bacteria and/or biofilm in between; or
8) combinations of 1) to 7), optionally with a non-chemical treatment; or
9) multiple repetitions of 1) to 8).

Bacteriophages (phages) are viruses, which infect only prokaryotic cells (cells without a nucleus), such as bacteria, while leaving mammalian (e.g. human) cells unharmed. These bacteriophages must be adapted to the specific type of bacteria that is to be removed. Reference is made to U.S. Pat. No. 8,168,419 (to Baldwin et al.), which discloses prevention and remediation of petroleum reservoir souring and corrosion by treatment with virulent bacteriophage. U.S. Pat. No. 8,168,419 describes how to prepare bacteriophages, and is hereby incorporated by reference in its entirety.

Exemplary chemical biocides may be selected from the list consisting of: glutaraldehyde, acrolein, quaternary ammonium compounds, 2,2-dibromo-3-nitrilopropionamide (DBNPA), tetrakis (Hydroxymethyl) Phosphonium Sulfate (THPS), 2.bromo-2-nitro-1,3-propanediol (Bronopol), formaldehyde, Dazomet, tributyl tetradecyl phosphonium chloride (TTPC), halogenated oxidizers.

Exemplary non-chemical treatments may be selected from the list consisting of: Nitrates, which promotes growth of nitrate reducing bacteria which may out-compete other unwanted bacteria, such as SRB or UV light, which may optionally be fitted to a pig tool, or other non-chemical treatments.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

In another aspect related to the foregoing there is provided the use of a hypotonic water for remediation of microbially induced corrosion in a section of a pipeline situated in connection with an oil reservoir or a section thereof, the pipeline being used to transport water with a total dissolved salt concentration of at least 0.25 M expressed as sodium chloride dissolved, the pipeline having a volume, where bacteria that induce corrosion grow on the inside surface of the pipeline and have an intracellular tonicity that is at least 3-fold higher than the hypotonic water.

EXAMPLES

Example 1

Cultures and Enrichment

Two enrichment cultures were used in this experiment, sulphate reducing bacteria (SRB) and methanogenic Archaea (MEA).

The sulphate reducing bacteria was enriched from a sample from Løgten Beach (Aarhus, Denmark) in media of marine salinity (around 35 ppt) specific for SRB. Methanogenic Archaea was obtained from a pure culture of *Methanosarcina acetivorans* (DSMZ) grown in media specific for this particular Archaea (Sowers, K. R., Baron, S. F., Ferry, J. G. 1984. *Methanosarcina acetivorans* sp. nov., an Acetotrophic Methane-Producing Bacterium Isolated from Marine Sediments. Appl. Environ. Microbiol. Vol. 47(5), 971).

Growth and activity in the SRB or MEA was measured by cell staining and counting (DAPI) and detection of either sulphide ($H_2S$) or methane ($CH_4$) production.

Setup

All experiments were carried out without $O_2$ contamination. Cultures of either SRB or MEA were filtered through a 0.22 μm poresize filter. Either pure anoxic water (no salts) or media of marine salinity specific for either SRB or MEA (control) was flushed through the filter whereby the cells were exposed to a short term (~one minute) pulse of hypotonic water (pure anoxic water) or media.

| Overview of the cell filtration and exposure to hypotonic water/media | |
|---|---|
| Cell membrane integrity | Viability |
| Liquids through the filter chamber Media ↓ Culture ↓ Hypotonic water or media ↓ | Liquids through the filter chamber Media ↓ Culture ↓ Hypotonic water or media ↓ |

-continued

| Overview of the cell filtration and exposure to hypotonic water/media | |
|---|---|
| Cell membrane integrity | Viability |
| Media ↓ Live/dead stain (incubate for 15 min in dark) ↓ Media ↓ Microscopic investigation | Media ↓ Move to incubation media ↓ Regular test of growth and activity |

Membrane Integrity

The cell membrane integrity was investigated by distinguishing between live and dead cells.

Following exposure to a pulse of either low-salinity water or media (control), a live/dead stain assay (LIVE/DEAD® BacLight™) was flushed through the filter and the filters were immediately analysed in a fluorescence microscope.

Viability Test

Following exposure to a pulse of either hypotonic water or media (control) the filters with cells were transferred to a flask with media specific for SRB or MEA, respectively and was incubated at 37° C. Re-growth was investigated by production of $H_2S$ or $CH_4$, respectively.

Results

A short pulse of anoxic fresh water resulted in a burst of both SRB and MEA cell membranes:

More dead SRB were visible when cells were exposed to a pulse of anoxic fresh water, compared to when cells were exposed to a pulse of SRB media.

Most of the visible MEA were dead after a short pulse of anoxic fresh water while mainly live cells of *M. acetivorans* was detectable after a short control pulse of MEA media.

Figure 2:
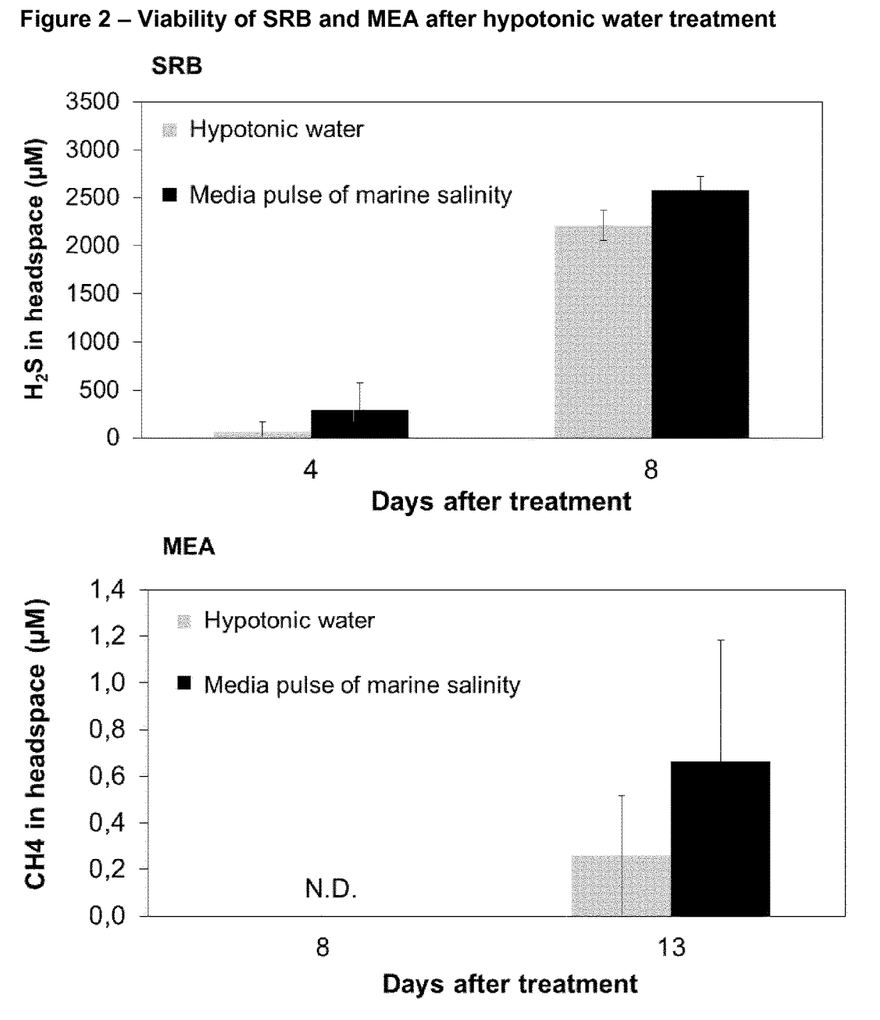
FIG. 2 shows regrowth of SRB (top) and MEA (bottom) measured by detection of $H_2S$ (SRB) or $CH_4$ (MEA) production (n=3).

Production of $H_2S$ by SRB and $CH_4$ by MEA was delayed after exposure to hypotonic water compared to a control experiment with a pulse of media (FIG. 2).

The results show that cultures of SRB and MEA were temporarily set back as a result of a short exposure to hypotonic water. Nevertheless, some cells survived the treatment and were able to establish a population within one (SRB) to two (MEA) weeks. A further hypotonic water treatment a few days after the first treatment may increase the potential for removal of MIC related microorganisms.

CONCLUSION

This experiment for testing the feasibility of utilizing hypotonic water as a tool for eliminating MIC related microorganisms, indicate that most but not all cells are killed by a hypotonic pulse of water and that regrowth of cells exposed to a hypotonic pulse is delayed.

The invention claimed is:

1. A method for remediation of microbially induced corrosion in a section of a pipeline used to transport water with a total dissolved salt concentration of at least 0.25 M expressed as sodium chloride dissolved, the pipeline having a volume, where halophilic or halotolerant bacteria that induce corrosion grow on the inside surface of the pipeline and that have an intracellular tonicity, the method comprising:

a) performing a pig run in the section of the pipeline;
b) subjecting the inside of the section of the pipeline to hypotonic water compared to the intracellular tonicity of the bacteria growing on the inside surface of the pipeline, the hypotonic water being sufficiently hypotonic to cause osmotic lysis in the bacteria, the hypotonic water having a total dissolved salt concentration of 5 mM or less expressed as sodium chloride dissolved, wherein the inside of the section of the pipeline is subjected to one or more pulses of hypotonic water which are enclosed by a plug on the leading end and the trailing end of the pulse of hypotonic water, and wherein the plug is liquid having a viscosity between 2-10 cP.

2. The method according to claim 1, where the bacteria are sulfate-reducing bacteria.

3. The method according to claim 1, wherein the section of the tube is in contact with hypotonic water for at least 30 seconds, at least 1 minute, at least 60 minutes.

4. The method according to claim 1, wherein the one or more pulses of hypotonic water each have a volume of 20% or less of the volume of the section of the pipeline.

5. The method according to claim 1, wherein the volume of the section of the pipeline is at least 15 m$^3$.

6. The method according to anyone of claim 1, wherein one or more additives are added to the hypotonic water, the one or more additives selected from the list consisting of: chemical biocides and/or bacteriophages.

* * * * *

UNITED STATES PATENT AND TRADEMARK OFFICE
CERTIFICATE OF CORRECTION

PATENT NO. : 10,344,905 B2  
APPLICATION NO. : 14/917475  
DATED : July 9, 2019  
INVENTOR(S) : Kristian Mogensen et al.

Page 1 of 1

It is certified that error appears in the above-identified patent and that said Letters Patent is hereby corrected as shown below:

On the Title Page

In (71) Applicant, delete "Copenhagen" and replace with --Kobenhavn--

In (72) Inventors, delete three (3) instances of "Copenhagen" and replace with --Kobenhavn--

Signed and Sealed this  
Eleventh Day of February, 2020

Andrei Iancu  
*Director of the United States Patent and Trademark Office*